US011285475B2

(12) United States Patent
Knowles et al.

(10) Patent No.: US 11,285,475 B2
(45) Date of Patent: Mar. 29, 2022

(54) DEVICE AND A METHOD FOR LABELLING A COMPONENT

(71) Applicant: Fluidic Analytics Limited, Cambridge (GB)

(72) Inventors: Tuomas Pertti Jonathan Knowles, Cambridge (GB); Sean Devenish, Cambridge (GB)

(73) Assignee: Fluidic Analytics Limited, Cambridge (GB)

(*) Notice: Subject to any disclaimer, the term of this patent is extended or adjusted under 35 U.S.C. 154(b) by 389 days.

(21) Appl. No.: 16/331,746

(22) PCT Filed: Sep. 11, 2017

(86) PCT No.: PCT/GB2017/052648
§ 371 (c)(1),
(2) Date: Mar. 8, 2019

(87) PCT Pub. No.: WO2018/046952
PCT Pub. Date: Mar. 15, 2018

(65) Prior Publication Data
US 2019/0344267 A1 Nov. 14, 2019

(30) Foreign Application Priority Data
Sep. 12, 2016 (GB) .................................. 1615456

(51) Int. Cl.
*G01N 1/00* (2006.01)
*B01L 3/00* (2006.01)
*G01N 33/533* (2006.01)

(52) U.S. Cl.
CPC ...... *B01L 3/502715* (2013.01); *G01N 33/533* (2013.01); *B01L 2400/0605* (2013.01); *B01L 2400/084* (2013.01)

(58) Field of Classification Search
CPC .... G01N 33/533; G01N 33/532; G01N 33/52; G01N 2458/00; B01L 3/5027
USPC .................. 422/82.08, 82.05; 436/176, 180
See application file for complete search history.

(56) References Cited

U.S. PATENT DOCUMENTS

| 3,718,432 A | 2/1973 | Roth |
| 9,952,222 B2 | 4/2018 | Yates et al. |
| 9,958,369 B2 | 5/2018 | Cohen et al. |
| 2009/0215023 A1* | 8/2009 | West .................. C12M 47/20 435/4 |
| 2017/0052147 A1 | 2/2017 | Herling et al. |
| 2018/0188145 A1 | 7/2018 | Mueller et al. |
| 2018/0267054 A1 | 9/2018 | Yates et al. |
| 2018/0328831 A1 | 11/2018 | Cohen et al. |

FOREIGN PATENT DOCUMENTS

| WO | WO 2017/141048 A1 | 8/2017 |
| WO | WO 2017/174975 A1 | 10/2017 |
| WO | WO 2018/002596 A1 | 1/2018 |
| WO | WO 2018/042190 A1 | 3/2018 |
| WO | WO 2018/046953 A1 | 3/2018 |
| WO | WO 2018/046954 A1 | 3/2018 |

OTHER PUBLICATIONS

International Search Report and Written Opinion for PCT/GB2017/052648 dated Nov. 27, 2017. 10 pages.
Cheng et al., Method for on-line derivatization and separation of aspartic acid enantiomer in pharmaceuticals application by the coupling of aspartic acid enantiomer in pharmaceuticals application by the coupling of flow injection with micellar electrokinetic chromatography. Journal of Chromatography A. Apr. 2005;1072(2):259-65.
Izquierdo et al., Simultaneous-fluorometric methods for the determination of ammonia and urea by use of flow injection configurations with dual injection valves. Fresenius' Journal of Analytical Chemistry. Jan. 1990;336(6):490-3.
Stevens et al., The stabilities of various thiol compounds used in protein purifications. Biochemical Education. Apr. 1983;11(2):70.
[No Author Listed], Quantitation of Total Protein Using OPA: Application Notes. Nature. May 30, 2006. Accessed Nov. 16, 2017 from <http://www.nature.com/app_notes/nmeth/2006/063006/full/an1781.html>.

* cited by examiner

*Primary Examiner* — Natalia Levkovich
(74) *Attorney, Agent, or Firm* — Wolf, Greenfield & Sacks, P.C.

(57) ABSTRACT

A device and method for fluorescent labelling a component is provided. The device comprising a first user-replaceable reservoir comprising a strongly buffered alkaline solution of aromatic ortho-dialdehyde dye, a second user-replaceable reservoir comprising a weakly buffered acidic solution of a reducing agent, one or more fluid pathways comprising the component, and a network of connection channels linking the reservoirs and the fluid pathway to enable the alkaline solution and the acidic solution to combine with the component in order to label the component by reacting the component with the alkaline solution and the acidic solution.

9 Claims, 4 Drawing Sheets

DEVICE AND A METHOD FOR LABELLING A COMPONENT

RELATED APPLICATIONS

This application is a national stage filing under 35 U.S.C. § 371 of international application number PCT/GB2017/052648, filed Sep. 11, 2017, which claims priority to GB application number GB1615456.9, filed Sep. 12, 2016, each of which is herein incorporated by reference in its entirety.

This invention relates to improvements in or relating to a device for labelling a component and in particular, a device for fluorescent labelling a biological or chemical component. The invention also relates to a method for fluorescent labelling a component in a mixture.

The use of fluorescent molecules in biological research is popular due to their versatility, sensitivity and quantitative capabilities. Fluorescent molecules, also called fluorophores, are able to respond absorb incident light and emit light at a specific wavelength different from the absorption wavelength, thereby allowing sensitive detection of the presence of the fluorophore.

In order to detect biological and/or chemical components, these components are typically labelled with fluorescent dyes. In one example, reacting biological components with a mixture comprising aromatic dialdehydes such as ortho-phthaldialdehyde (OPA) dye, and a reducing agent such as β-mercaptoethanol (BME), can fluorescently label the components. The use of OPA as a labelling agent is well established and was first reported in the early 1970's. OPA dyes are often used for assaying amino groups of biological molecules. More specifically, OPA yields fluorescently labelled biomolecules by reacting with primary amine groups of protein or peptide fragments in the presence of thiols in solution.

OPA/BME labelling reactions occur at high pH however, atmospheric oxygen has been known to cause BME to oxidise rapidly and the rate of BME oxidation is elevated at high pH. As a consequence, the functional life of the reactive dye is limited. Therefore, labelling experiments using OPA/BME mixture can only be performed over a short period of time i.e. approximately a week.

The short life-span of OPA/BME mixture can be problematic for labelling experiments that are performed in a remote location, such as a user operated device which may not be operated immediately. Likewise, the provision of a reactive OPA dye solution that does not require the user to manually add BME shortly prior to use is impractical.

It is against this background that the invention has arisen.

According to the present invention there is provided, a method for fluorescent labelling a component in a mixture, the method comprising the steps of a) providing a strongly buffered alkaline solution of aromatic ortho-dialdehyde dye in a first reservoir;

b) providing a weakly buffered acidic solution of reducing agent in a second reservoir;

c) providing a component in a fluid pathway, wherein the fluid pathway is connected to the first and second reservoirs by a network of connection channels;

d) flowing the alkaline solution and the acidic solution through the network of connection channels to combine with the component in order to label the component by reacting the component with the aromatic ortho-dialdehyde dye and the reducing agent.

Storing the aromatic ortho-dialdehyde dye and the reducing agent in separate reservoirs allows for experimental conditions to be optimised in each reservoir prior to mixing the aromatic ortho-dialdehyde dye and the reducing agent together. For example, the strongly buffered alkaline solution in the first reservoir is provided at a high pH, which is suitable for a labelling reaction.

In contrast, the weakly buffered acidic solution in the second reservoir is optimised to be at a low pH, which reduces the rate of oxidation of the reducing agent caused by atmospheric air.

In some embodiments, step (d) may comprise combining the alkaline solution and the acidic solution and subsequently reacting the component with the alkaline solution and the acidic solution.

In other embodiments, step (d) may comprise combining the alkaline solution with the component and subsequently introducing the acidic solution.

In some embodiments, step (d) may comprise combining the acidic solution with the component and subsequently introducing the alkaline solution.

The strongly buffered alkaline solution and the weakly buffered acidic solution may be combined together to provide an overall pH of an alkaline solution. The overall pH of an alkaline solution may provide suitable conditions for the fluorescent labelling of a component.

In some embodiments, the acidic solution may increase the functional life of the reducing agent by up to 50 to 100 days, or it may exceed 40, 60, 80 or 100 days.

In some embodiments, the acidic solution may increase the functional life of the reducing agent by less than 100, 80, 60 or 40 days. Preferably, the acidic solution increases the functional life of the reducing agent by around 75 days.

The method disclosed by the present invention may further comprise providing an anti-oxidant additive, which is configured to stabilise the reducing agent. The addition of the anti-oxidant additive can increase the functional life of the reducing agent by around 500 to 1000 days, or it may increase the functional life of the reducing agent by 200, 300, 400, 500, 600, or 800 days. In some embodiments, the additive may increase the functional life of the reducing agent by less than 1000, 800, 600, 400, 200 or 100 days. Preferably, the addition of the antioxidant additive increases the functional life of the reducing agent by around 500 days.

In some embodiments, the acidic solution may have a pH range of between 1 to 7, 2 to 6, 3 to 6, 4 to 6 or 5 to 6. Preferably, the pH range of the acidic solution is 2 to 6.

In some embodiments, the alkaline solution may have a pH range of between 7 to 14, 8 to 14, 9 to 14, 10 to 14, 11 to 14, 12 to 14, or 13 to 14. Preferably, the pH range of the alkaline solution is 8 to 14.

The component may be a biological or chemical component. For example, the biological or chemical component can be a peptide, a protein or a nucleic acid. In some embodiments, the component may be an amine group of a protein or a peptide.

In some embodiments, the aromatic ortho-dialdehyde dye is ortho-phthaldialdehyde (OPA) dye. OPA dyes are sensitive fluorescent dyes, which can be used for assaying amine groups in solution, notably in peptide fragments, proteins and amino acids.

In some embodiments, the reducing agent may be β-mercaptoethanol (BME). BME can be used to react with OPA efficiently.

The additive may be selected from ascorbate, isoacorbate, or lactate. Preferably, the additive is a lactate salt.

According to another aspect of the invention there is provided, a device for fluorescent labelling a component, the device comprising, a) a first user-replaceable reservoir comprising a strongly buffered alkaline solution of aromatic ortho-dialdehyde dye,
b) a second user-replaceable reservoir comprising a weakly buffered acidic solution of a reducing agent,
c) one or more fluid pathways comprising the component, and
d) a network of connection channels linking the reservoirs and the fluid pathway to enable the alkaline solution and the acidic solution to combine with the component in order to label the component by reacting the component with the alkaline solution and the acidic solution.

The network of connection channels may be configured to combine the alkaline solution and the acidic solution before combining the resulting mixture with the component.

In some embodiments, the network of connection channels may be configured to combine the alkaline solution with the component before combining the resulting mixture with the acidic solution.

In other embodiments, the network of connection channels may be configured to combine the acidic solution with the component before combining the resulting mixture with the alkaline solution.

The second reservoir may further comprise an antioxidant additive configured to stabilise the reducing agent.

In some embodiments, the second reservoir may be gas impermeable. In some embodiments, the first reservoir may be light impermeable. The gas and light impermeable reservoirs provided may be advantageous as it can improve the storage life of the reagent.

The network of connection channels may be provided with one or more one way valves, which may be used to prevent reverse flow of the alkaline solution and/or the acidic solution.

In some embodiments, the downstream hydrodynamic resistance of each connection channel may be substantially equal so that the flow rates of the solutions from the first and second reservoirs into the fluid pathways are substantially equal.

In some embodiments, the downstream hydrodynamic resistance of each connection channel may be substantially different so that the flow rates of the solutions from the first and second reservoirs into the fluid pathways are substantially different.

Preferably, the fluid pathways are provided on a microfluidic device.

The invention will now be further and more particularly described, by way of example only, and with reference to the accompanying drawings, in which:

FIG. 1a provides an overview of a device according to the present invention,

FIG. 1b illustrates a further embodiment of the device according to FIG. 1a,

Figure 3:
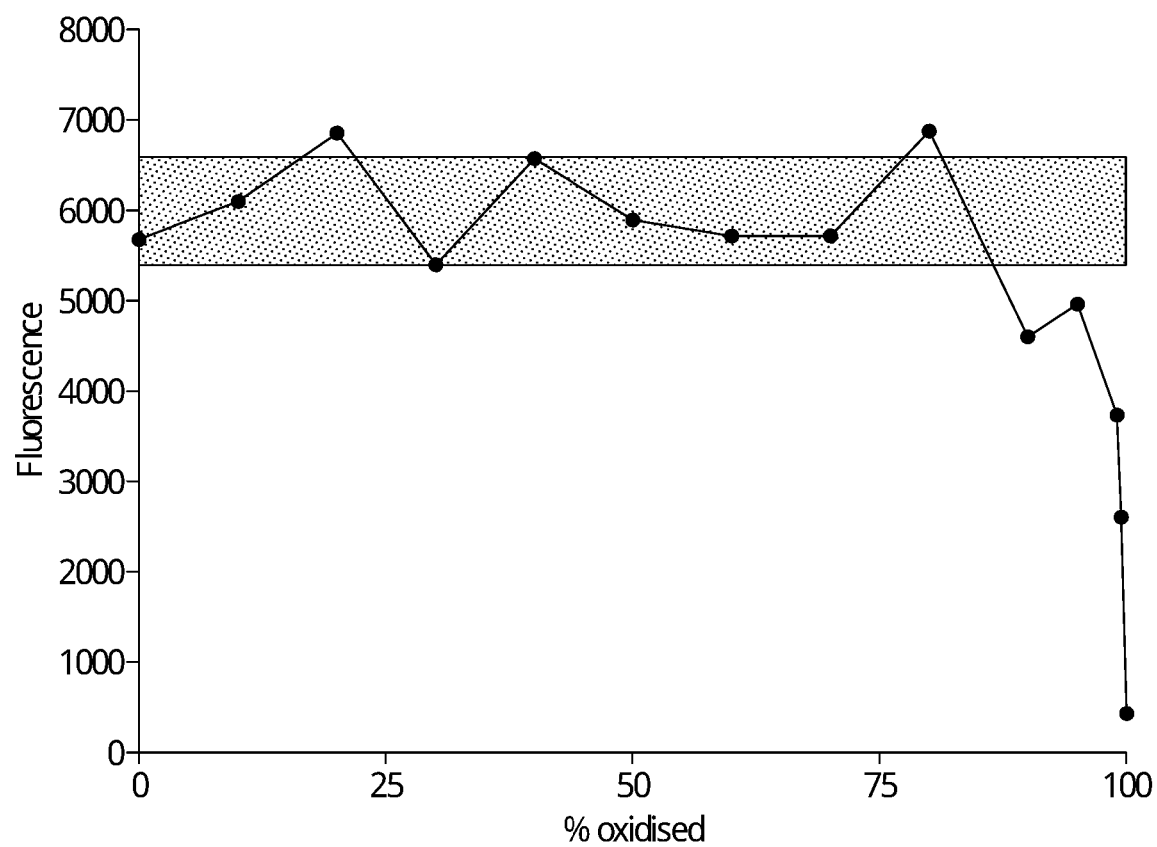

FIG. 3 provides data showing the effects of BME oxidation, and

Figure 4:
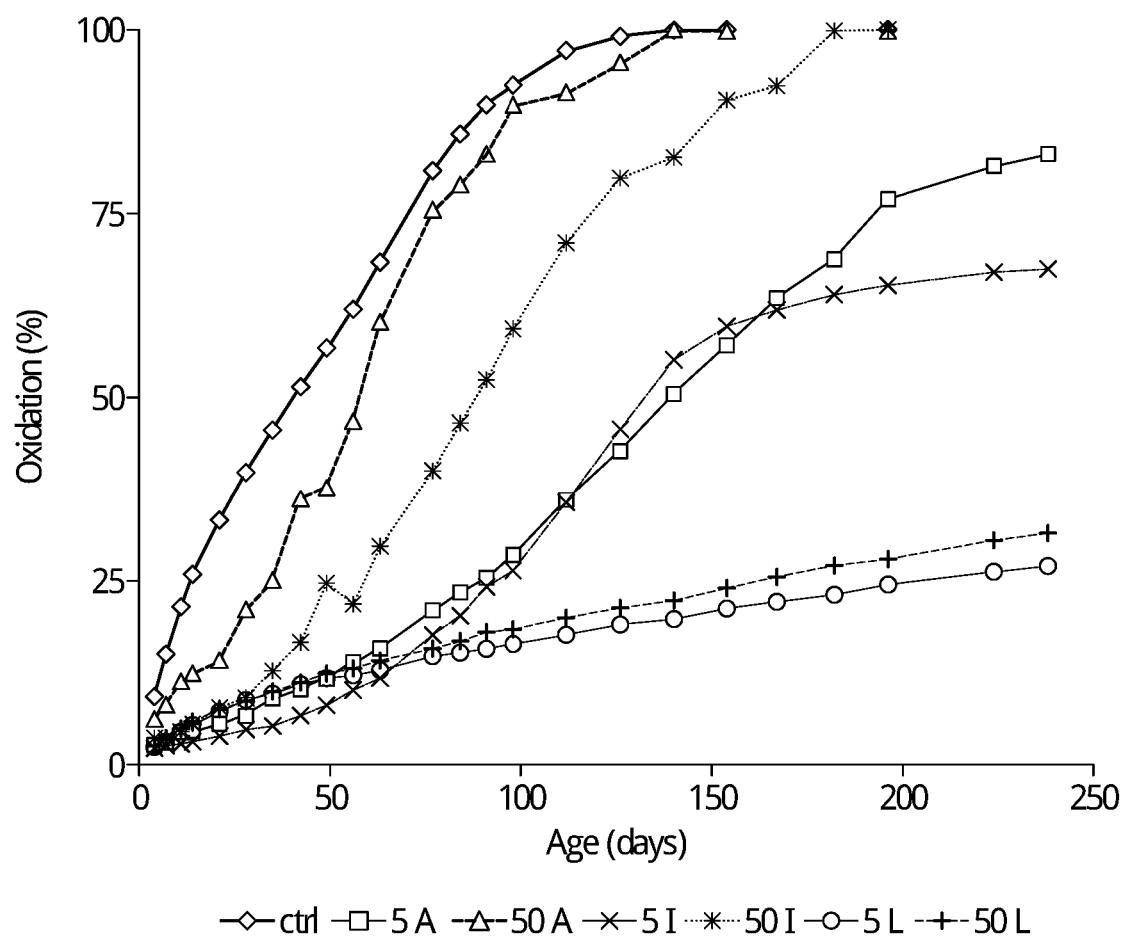

FIG. 4 showing the inhibition of BME oxidation by an antioxidant additive.

Figure 1A:
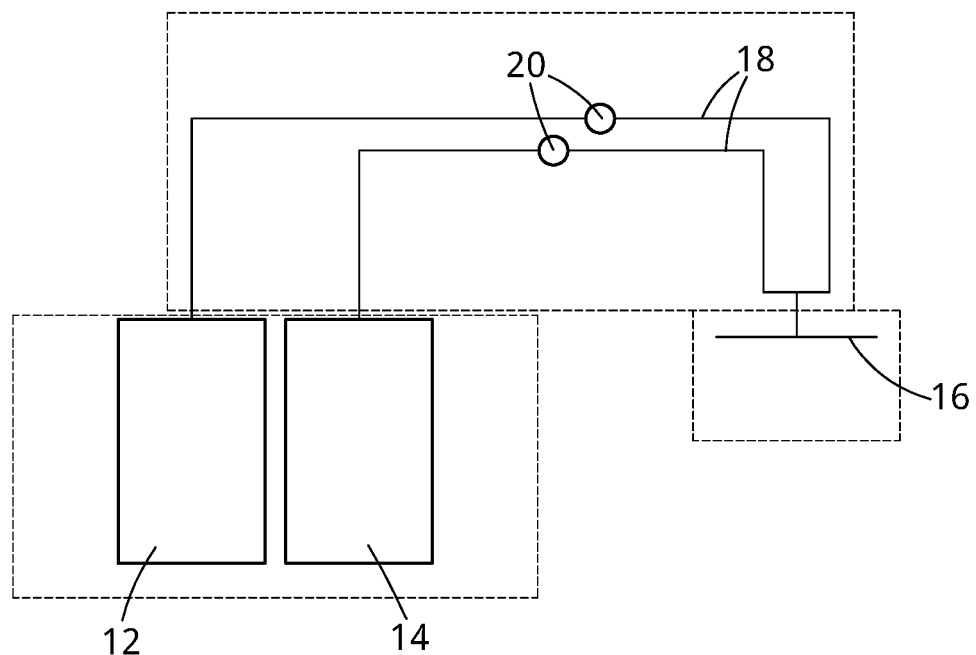
Figure 1B:
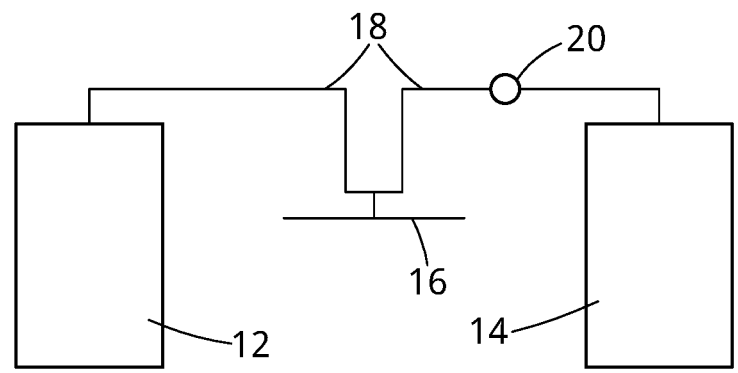

Referring to FIGS. 1a and 1b there is provided a device 10 for fluorescent labelling a component. The device 10 comprises a first reservoir 12 comprising a strongly buffered alkaline solution of aromatic ortho-dialdehyde dye such as OPA, and a second reservoir 14 comprising a weakly buffered acidic solution of a reducing agent for example, BME.

The first and second reservoirs may form a reagent cartridge that may be coupled to the connection channels by a user.

Strongly buffered alkaline solution may be prepared at a concentration of between 100 mM to 1000 mM. Additionally, the weakly buffered acidic solution can be prepared at a concentration of between 0.5 mM to 50 mM. The aromatic ortho-dialdehyde dye may be prepared at a concentration between 0.5 mM to 20 mM. Moreover, the reducing agent may be prepared at a concentration of 1 to 50 mM.

Referring to FIGS. 1a and 1b, the reservoirs provide an impermeable barrier. The first reservoir is impermeable to light and the second reservoir is impermeable to gas, which may help increase the storage or shelf-life of the reagents within the reservoirs. The reservoirs prevent the acidic solution mixing with the alkaline solution prior to use. The reservoirs are made with aluminised film, such as a foil-lined coating/pouch or other barrier layers.

An antioxidant additive is added into the second reservoir which stabilises the BME by around 500 to 1000 days. The concentration of the antioxidant additives added to the reservoir ranges from 0.5 mM to 100 mM. The antioxidant additive can be a lactate salt such as a potassium lactate or a sodium lactate.

The device further comprises one or more fluid pathways 16, which is configured to comprise a component such as a biological or chemical component. The biological or chemical component can be a protein, peptide or nucleic acid. One or more fluid pathways may be provided on a fluidic device such as a microfluidic device.

As illustrated in FIGS. 1a and 1b, a network of connection channels 18 is provided by the device 10. The network of connection channels 18 is configured to allow the combination of the acidic solution, the alkaline solution and the component. Referring to FIGS. 1a and 1b, the network of connection channels 18 is configured to link the first reservoir 12, the second reservoir 14 and the fluid pathway 16 together in order to enable the alkaline solution, the acidic solution and the component to combine.

The network of connection channels may be used to combine the flow of the alkaline solution and the flow of the acidic solution before combining the resulting mixture with the component. Alternatively, the network of connection channels may be used to combine the flow of the alkaline solution with the component before combining the resulting mixture with the flow of the acidic solution. Alternatively, the network of connection channels may be configured to combine the flow of the acidic solution with the component before combining the resulting mixture with the flow of the alkaline solution.

The strongly buffered alkaline solution in the first reservoir 12 and the weakly buffered acidic solution in the second reservoir 14 is combined together to provide an overall pH of an alkaline solution. The high pH of the combined solution can provide suitable conditions for effective fluorescent labelling of the component.

The labelling of the component occurs by reacting the component with the alkaline solution and the acidic solution. More specifically, the labelling of the component occurs by reacting the component with the aromatic ortho-dialdehyde dye and the reducing agent. For example, the combination of OPA and BME can be used to fluorescently label the amine group of a biological molecule such as a peptide or protein. More explicitly, the combination of OPA and BME can be used to fluorescently label the amine group of a lysine residue and/or the N-terminal amine of a peptide chain.

As illustrated in FIGS. 1a and 1b, the network of connection channels 18 is provided with one or more one way valves 20, which are configured to prevent the reverse flow of the alkaline solution and/or the acidic solution. For example, the one way valves can prevent the flow of the alkaline and/or the acidic solution from the connection channels, the fluid pathways or both, into the first and second reservoirs.

The hydrodynamic resistances of each connection channel are dictated by the geometry of the connection channel, such as the cross sectional area of the channel, the length of the channel, and the surface roughness of the channel.

The downstream hydrodynamic resistance of each connection channel may be substantially equal so that the flow rates of the solutions from the first and second reservoirs into the fluid pathways are substantially equal. This may provide a continuous flow of the solutions from the first and second reservoirs into the fluid pathways. Alternatively, the downstream hydrodynamic resistance of each connection channel may be substantially different so that the flow rates of the solutions from the first and second reservoirs into the fluid pathways are substantially different.

Figure 2:
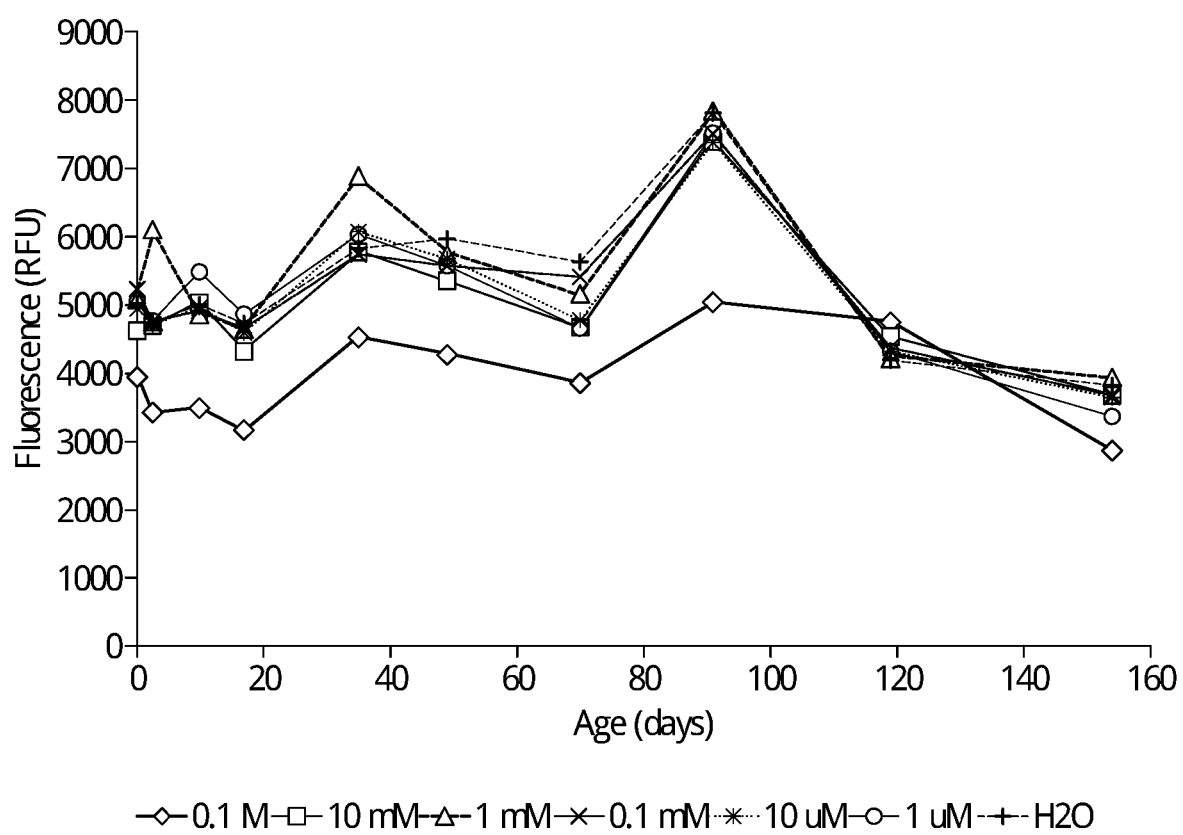
FIG. 2 shows the functional activity of BME under acidic conditions.

Referring to FIG. 2, there is data showing the function of BME at different levels of acidity in the OPA labelling reaction. The experiment as shown in FIG. 2 investigated the effect of reducing the pH of the BME solution on the long term storage life of BME. A series of BME solutions (12 mM in water) may be prepared and these solutions may be acidified with varying concentrations of added acetic acid, from 0.1 M to 1 uM, covering a pH range from ~2 to ~6.

Two control samples may also be set up consisting of no added acid (ie water only. The solutions can be stored in non-gas tight microtubes in the dark and tested for function periodically over five months by testing the fluorescence yield when reacted with bovine serum albumin (BSA, 330 nM) and OPA. The results in FIG. 2 illustrates that the acidified BME solution provides a consistent reaction up to about 75 days, after which it becomes more erratic with a generally decreasing trend in functional activity. It was also found, although not illustrated in the accompanying figures, that the reagent high pH BME remains active for about seven days depending on the exact conditions.

Referring to FIG. 3, the data shows the effects of BME oxidation on the function of a fluorescent dye. The experiment illustrated in FIG. 3 investigated the effect of known degrees of BME oxidation on the function of the OPA dye. A series of BME solutions can be made up by combining fresh BME with 2-hydroxyethyl disulfide (HED) in varying proportions to produce a series of BME solutions with known degrees of oxidation. The function of these solutions may then be determined by labelling bovine serum albumin (BSA, 330 nM, 50 uL) with the BME test solutions (25 uL) and OPA (3 mM, 25 uL) and measuring the fluorescence of the product.

The data in FIG. 3 shows BME oxidation of up to about 80% is tolerated before the fluorescent dye performance decreases significantly. In some instances, the performance of the fluorescent dye may also be sensitive to the concentration of the amine being labelled. A subsequent experiment (not illustrated in the drawings) using more concentrated BSA (4 uM) indicated similar results, with 75% oxidised BME giving the same level of fluorescence as 0% oxidised BME. The next higher level of oxidation tested, at 90%, showed a significant drop-off in fluorescence.

Referring to Table 1 there is shown experimental data that demonstrates the rate of BME oxidation in the presence of an antioxidant additive. A series of antioxidants (5 and 50 mM) can be mixed with the BME and tested for compatibility with the OPA labelling reaction. Reactions consisted of 50 uL of sample (protein, bovine serum albumin (BSA), or small amine, N-acetyllysine (NAK)), 25 uL OPA solution and 25 uL BME solution.

An antioxidant can be selected on the basis that it does not significantly change the measured fluorescence against a test sample, which may be defined as less than 10% variation; and/or it does not measurably slow the reaction, which can be defined as no delay in reaching maximum fluorescence when performing manual measurements on a plate reader, where the first reading is taken at about 15 seconds after mixing.

| Amine | Antioxidant | Conc (mM) | Max Fluorescence | Time to max | Fluorescene at t = 0 sec | Fluorescene at t = 120 sec |
|---|---|---|---|---|---|---|
| NAK | None | 0 | 7180 | 0 | 7180 | 6510 |
| | (DMSO ctrl) | 0 | 10000 | 0 | 10000 | 9050 |
| | Ascorbic acid | 50 | 6690 | 0 | 6690 | 5990 |
| | Ascorbic acid | 5 | 7300 | 0 | 7300 | 6470 |
| | a-tocopherol | 50 | 4400 | 0 | 4400 | 4220 |
| | a-tocopherol | 5 | 5620 | 0 | 5620 | 5370 |
| | Isoascorbic acid | 50 | 6330 | 10.3 | 6130 | 6000 |
| | Isoascorbic acid | 5 | 7000 | 0 | 7000 | 6370 |
| | Sodium lactate | 50 | 7120 | 0 | 7120 | 6400 |
| | Sodium lactate | 5 | 7120 | 0 | 7120 | 6420 |
| | Citric acid | 50 | 6570 | 70 | 3830 | 6440 |
| | Citric acid | 5 | 7230 | 0 | 7230 | 6500 |
| | Sodium azide | 50 | 6870 | 0 | 6870 | 6240 |
| | Sodium azide | 5 | 7010 | 4.2 | 6970 | 6420 |
| | Melatonin | 50 | 10400 | 0 | 10400 | 9610 |
| | Melatonin | 5 | 9830 | 0 | 9830 | 9270 |
| BSA | None | 0 | 5080 | 0 | 5080 | 4910 |
| | (DMSO ctrl) | 0 | 5830 | 0 | 5830 | 5100 |
| | Ascorbic acid | 50 | 4410 | 91 | 4190 | 4400 |
| | Ascorbic acid | 5 | 5620 | 0 | 5620 | 5100 |
| | a-tocopherol | 50 | 3460 | 0 | 3460 | 3390 |
| | a-tocopherol | 5 | 4830 | 81 | 4280 | 4790 |
| | Isoascorbic acid | 50 | 4800 | 15 | 4520 | 4580 |
| | Isoascorbic acid | 5 | 5150 | 0 | 5150 | 4610 |
| | Sodium lactate | 50 | 5480 | 80 | 5160 | 5270 |
| | Sodium lactate | 5 | 6210 | 82 | 5910 | 6110 |
| | Citric acid | 50 | 4620 | 120 | 3010 | 4620 |
| | Citric acid | 5 | 5180 | 69 | 5050 | 4660 |

-continued

| Amine | Antioxidant | Conc (mM) | Max Fluorescence | Time to max | Fluorescence at t = 0 sec | Fluorescene at t = 120 sec |
|---|---|---|---|---|---|---|
| | Sodium azide | 50 | 5430 | 0 | 5430 | 5020 |
| | Sodium azide | 5 | 5320 | 0 | 5320 | 4930 |
| | Melatonin | 50 | 7280 | 0 | 7280 | 6320 |
| | Melatonin | 5 | 6560 | 0 | 6560 | 5490 |

The ability of the antioxidants that have been found to be compatible with the OPA/BME dye reaction to prevent the oxidation of BME under the required conditions can be analysed by nuclear magnetic resonance (NMR) spectrometry. Samples of BME may be prepared in 10 uM AcOH/ D20 (5 uL in 10 uL D20) or at a higher concentration for NMR analysis. Samples of BME can be prepared comprising different anti-oxidant additives for example; ascorbate, isoascorbate, and lactate may be prepared at 5 mM and 50 mM concentrations. The samples may be stored in glass NMR tubes that are capped with tight fitting (but not gas-impermeable) plastic caps. Alternatively, the samples can be stored in a shigemi tubes, 3 mm, 5 mm or 10 mm NMR tubes. Samples may then be placed into an NMR instrument for measurement to produce NMR spectra, such as a 1D, 2D or 3D spectra. The experiments may be performed on a 400, 600 or 800 MHz NMR instrument.

As illustrated in FIG. 4, lactate shows the greatest inhibition of BME oxidation followed by isoascorbate, whereas ascorbate shows the least inhibition of oxidation. The lower concentration of anti-oxidant (5 mM) shows better performance than the higher concentration (50 mM) in all cases.

It will further be appreciated by those skilled in the art that although the invention has been described by way of example with reference to several embodiments, it is not limited to the disclosed embodiments and that alternative embodiments could be constructed without departing from the scope of the invention as defined in the appended claims.

The invention claimed is:

1. A method for fluorescent labelling a component in a mixture, the method comprising the steps of
    a) providing a buffered alkaline solution at a pH of between 8 and 14 of aromatic ortho-dialdehyde dye in a first reservoir;
    b) providing a buffered acidic solution at a pH of between 2 and 6 of a thiol based reducing agent in a second reservoir further comprising an antioxidant additive configured to stabilize the reducing agent;
    c) providing a component in a fluid pathway, wherein the fluid pathway is connected to the first and second reservoirs by a network of connection channels;
    d) flowing the alkaline solution and the acidic solution through the network of connection channels to combine with the component in order to label the component by reacting the component with the aromatic ortho-dialdehyde dye and the reducing agent.

2. The method according to claim 1, wherein step (d) comprises combining the alkaline solution and the acidic solution and subsequently reacting the component with the alkaline solution and the acidic solution.

3. The method according to claim 1, wherein step (d) comprising combining the alkaline solution with the component and subsequently introducing the acidic solution.

4. The method according to claim 1, wherein step (d) comprises combining the acidic solution with the component and subsequently introducing the alkaline solution.

5. The method according to claim 1, wherein the component is a biological or chemical component.

6. The method according to claim 1, wherein the component is a peptide, a protein or a nucleic acid or an amine group of a protein or a peptide.

7. The method according to claim 1, wherein the aromatic ortho-dialdehyde dye is OPA.

8. The method according to claim 1, wherein the reducing agent is BME.

9. The method according to claim 1, wherein the additive is selected from ascorbate, isoascorbate, or lactate.

* * * * *